(12) United States Patent  (10) Patent No.: US 8,777,859 B2
Kim et al.  (45) Date of Patent: Jul. 15, 2014

(54) METHOD AND APPARATUS FOR PROCESSING ULTRASOUND IMAGE

(75) Inventors: Yun-tae Kim, Hwaseong-si (KR); Jung-ho Kim, Yongin-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 68 days.

(21) Appl. No.: 13/545,634

(22) Filed: Jul. 10, 2012

(65) Prior Publication Data

US 2013/0018265 A1  Jan. 17, 2013

(30) Foreign Application Priority Data

Jul. 11, 2011 (KR) .................. 10-2011-0068554

(51) Int. Cl.
*A61B 8/00* (2006.01)
*G06K 9/00* (2006.01)
(52) U.S. Cl.
USPC .......................................... 600/443; 382/128
(58) Field of Classification Search
USPC ................... 600/437, 443, 444; 382/128
See application file for complete search history.

(56) References Cited

U.S. PATENT DOCUMENTS

| | | | |
|---|---|---|---|
| 5,497,777 | A | 3/1996 | Abdel-Malek et al. |
| 2010/0228129 | A1 | 9/2010 | Osumi |

FOREIGN PATENT DOCUMENTS

| | | |
|---|---|---|
| JP | 2005-296331 A | 10/2005 |
| KR | 10-2006-0034003 A | 4/2006 |
| KR | 10-2009-0041475 A | 4/2009 |

*Primary Examiner* — Michael Rozanski
(74) *Attorney, Agent, or Firm* — NSIP Law

(57) ABSTRACT

A method of processing an ultrasound image includes generating a plurality of two-dimensional (2D) ultrasound images from three-dimensional (3D) ultrasound volume data of an object to be diagnosed, generating a plurality of tissue edge images of an edge of at least one tissue component in the object to be diagnosed based on values of a plurality of pixels forming each of the 2D ultrasound images generated from the 3D ultrasound volume data, and generating a 2D ultrasound image from which a noise component has been removed by discriminating the edge of the at least one tissue component from a position of the noise component based on a difference between a similarity of the edge of the at least one tissue component in the tissue edge images and a similarity of the noise component in the tissue edge images.

20 Claims, 12 Drawing Sheets

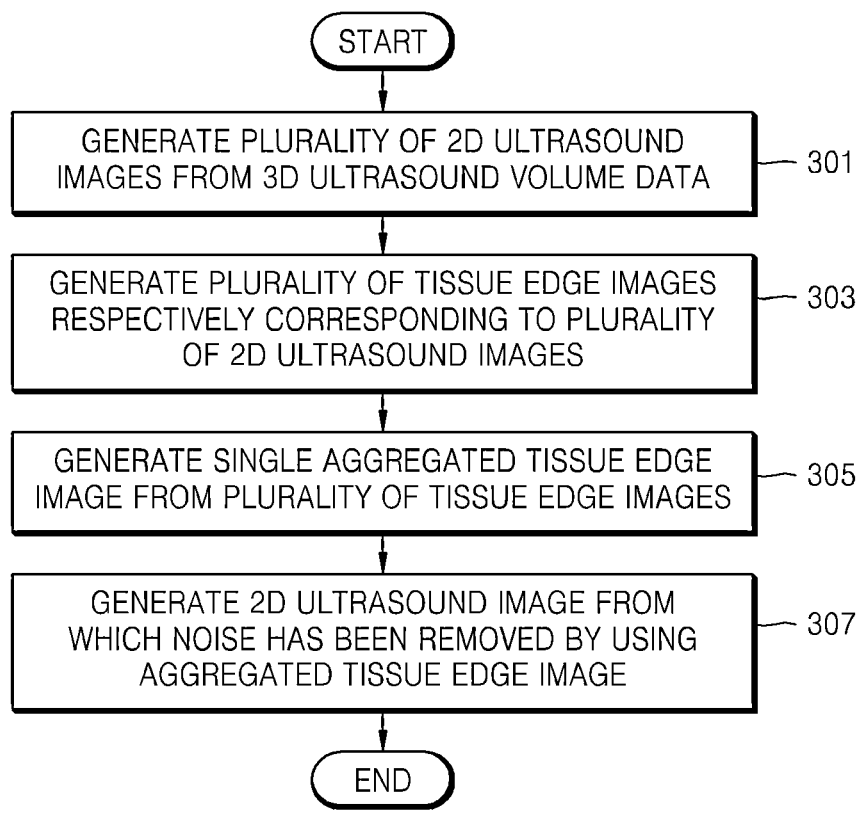

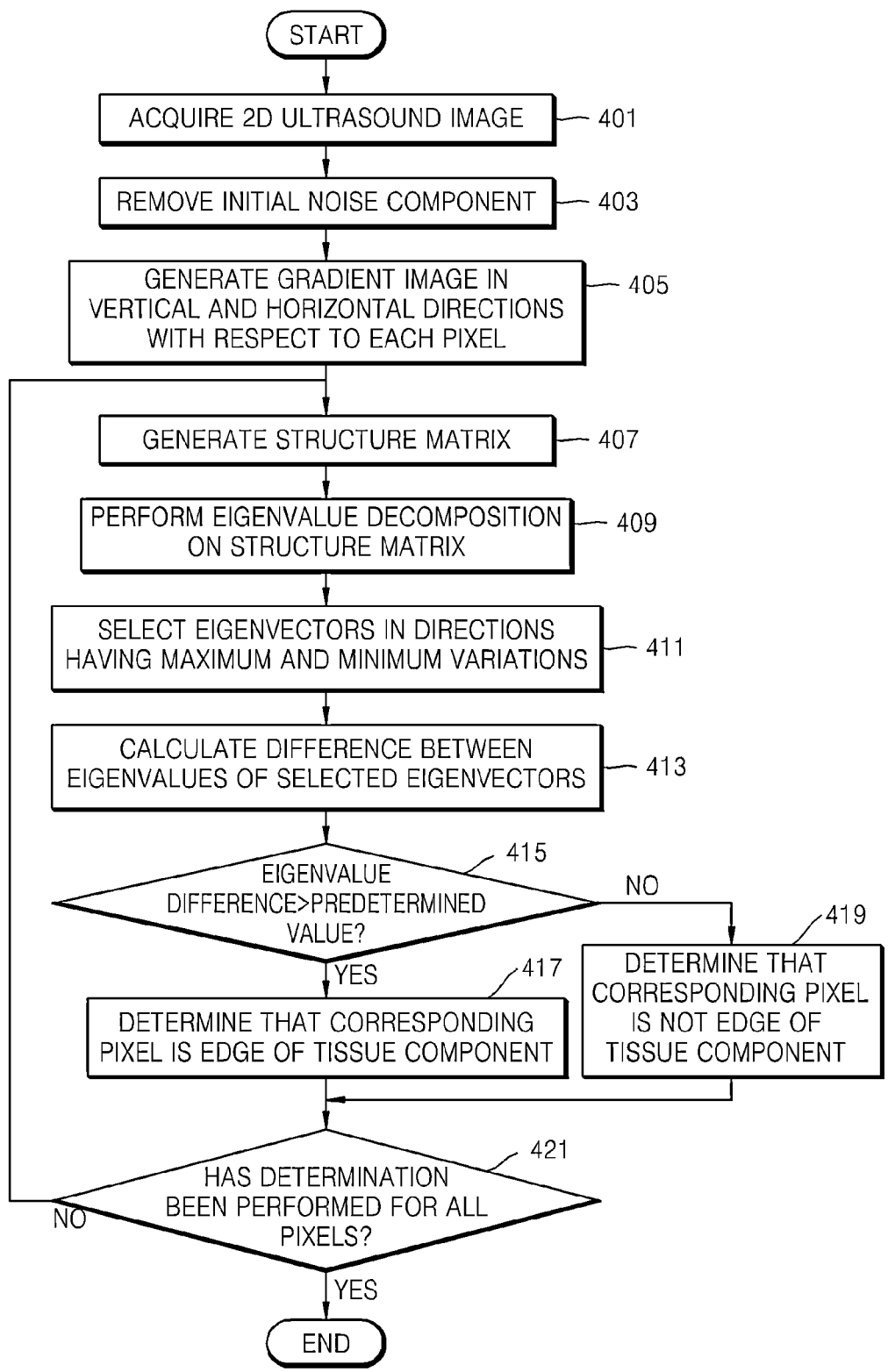

FIG. 5A
FIG. 5B
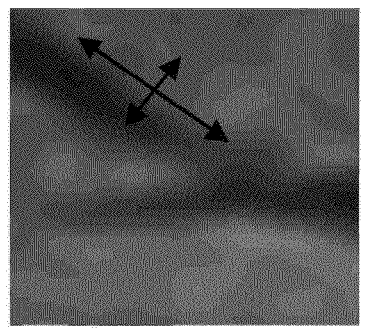
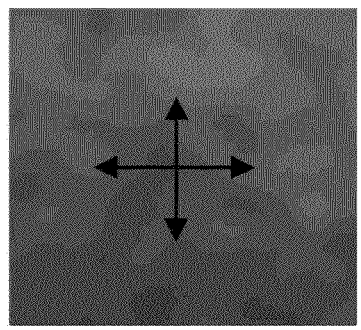
FIG. 6
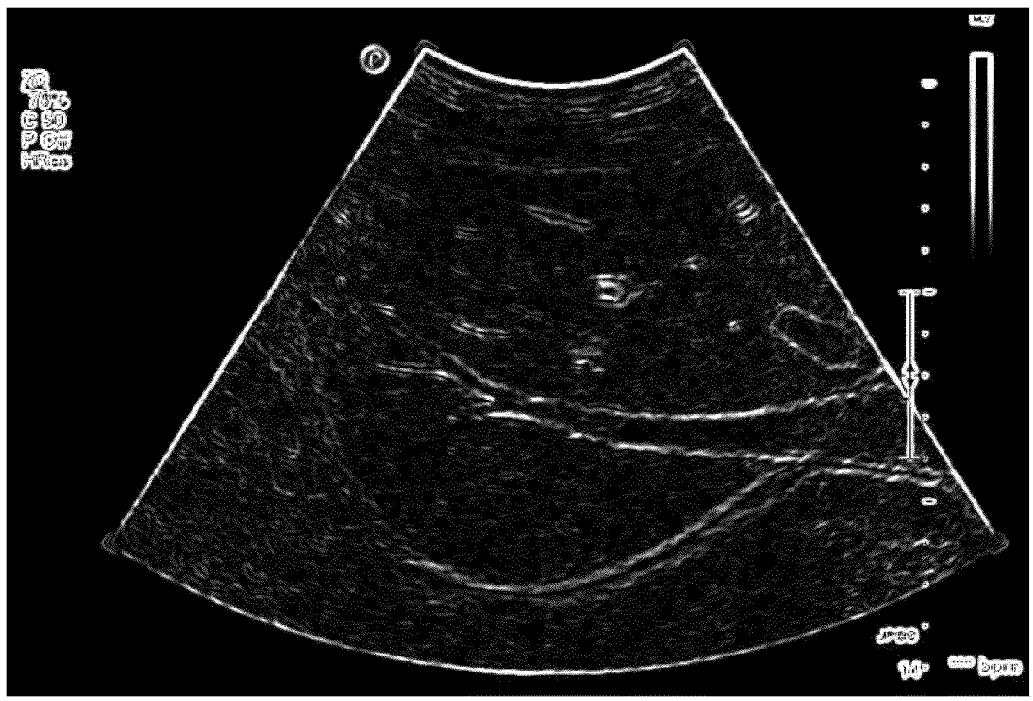

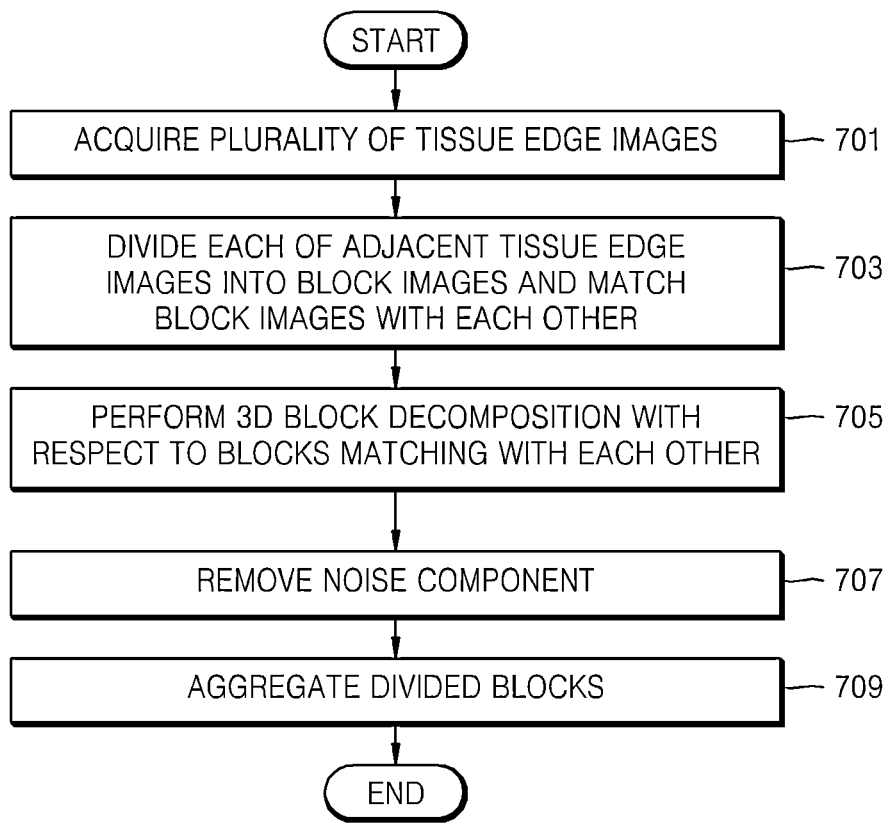

FIG. 8A
FIG. 8B
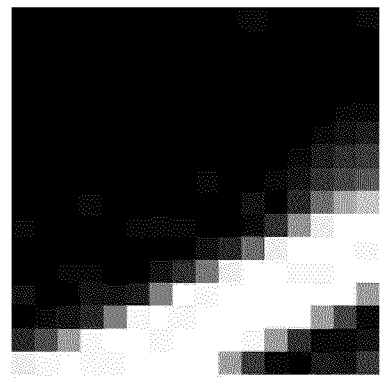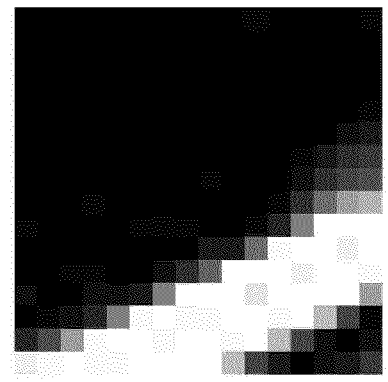
FIG. 9A
FIG. 9B
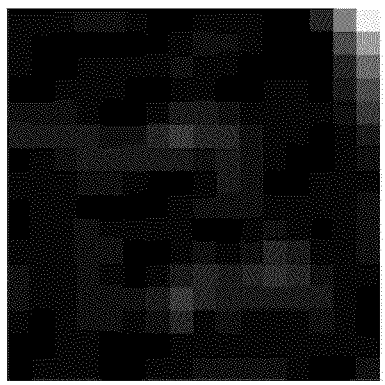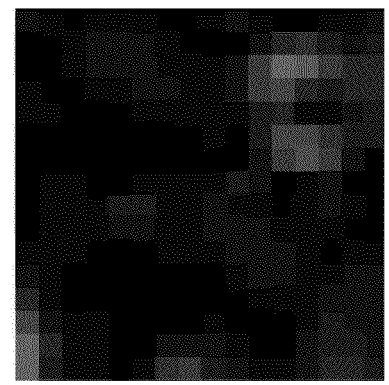

METHOD AND APPARATUS FOR PROCESSING ULTRASOUND IMAGE

CROSS-REFERENCE TO RELATED APPLICATIONS

This application claims the benefit of Korean Patent Application No. 10-2011-0068554 filed on Jul. 11, 2011, in the Korean Intellectual Property Office, the disclosure of which is incorporated herein by reference in its entirety.

BACKGROUND

1. Field

This disclosure relates to methods and apparatuses for processing an ultrasound image by acquiring a plurality of ultrasound images from three-dimensional ultrasound volume data and post-processing the acquired ultrasound images to clarify the ultrasound image.

2. Description of Related Art

Recently, diagnosis equipment using ultrasound images have been widely used. Diagnostic ultrasound imaging equipment forms and provides an image of an object to be diagnosed, e.g., an organ, by radiating ultrasonic waves onto the object to be diagnosed and detecting and processing ultrasonic waves reflected from the object to be diagnosed. The diagnostic ultrasound imaging equipment allows real time medical treatment and does not harm human bodies. However, the diagnostic ultrasound imaging equipment provides a lower image quality than other medical diagnosis equipment because of a low degree of definition due to noise, particularly speckle noise. The speckle noise is noise caused by an interference phenomenon among ultrasonic wavelengths, and appears as a spot in an ultrasound image. The image quality of ultrasound images is degraded by the speckle noise, and accuracy in perceiving an important part such as a boundary between an object to be diagnosed and a background is lowered.

Previously, research has been conducted on methods of removing noise from an ultrasound image by applying an arbitrary threshold value to a single two-dimensional ultrasound image to enhance an image quality of the ultrasound image that has been degraded by the noise.

SUMMARY

In one general aspect, a method of processing an ultrasound image includes generating a plurality of two-dimensional (2D) ultrasound images from three-dimensional (3D) ultrasound volume data of an object to be diagnosed; generating a plurality of tissue edge images of an edge of at least one tissue component in the object to be diagnosed based on values of a plurality of pixels forming each of the 2D ultrasound images generated from the 3D ultrasound volume data; and generating a 2D ultrasound image from which a noise component has been removed by discriminating the edge of the at least one tissue component from a position of the noise component based on a difference between a similarity of the edge of the at least one tissue component in the tissue edge images and a similarity of the noise component in the tissue edge images.

The generating of the 2D ultrasound image from which the noise component has been removed may include identifying the edge of the at least one tissue component based on the difference between the similarity of the edge of the at least one tissue component in the tissue edge images and the similarity of the noise component in the tissue edge images; generating, from the tissue edge images, an aggregated tissue edge image from which the noise component has been removed; and removing the noise component from one of the 2D ultrasound images generated from the 3D ultrasound volume data based on the aggregated tissue edge image.

The plurality of 2D ultrasound images may include a reference ultrasound image from which the noise component is to be removed, and a first ultrasound image and a second ultrasound image adjacent to the reference ultrasound image; and the plurality of tissue edge images may include a reference tissue edge image corresponding to the reference ultrasound image, and a first tissue edge image and a second tissue edge image adjacent to the reference tissue edge image.

The generating of the aggregated tissue edge image may include dividing the tissue edge images into blocks each having a predetermined size; matching blocks in the reference tissue edge image with corresponding blocks in the first tissue edge image, and with corresponding blocks in the second tissue edge image; discriminating blocks of the reference tissue edge image including the edge of the at least one tissue component from blocks of the reference tissue edge image not including the edge of the at least one tissue component based on the difference between the similarity of the edge of the at least one tissue component and the similarity of the noise component in the matching blocks; removing the noise component from the blocks of the reference tissue edge image not including the edge of the at least one tissue component; and aggregating the blocks of the reference tissue edge image including the edge of the at least one tissue component and the blocks of the reference tissue edge image from which the noise component has been removed to generate the aggregated tissue edge image.

The matching of the blocks may include determining that a block in the reference tissue edge image matches a corresponding block in the first tissue edge image or the second tissue edge image if a normalized cross-correlation (NCC) indicating a similarity between the two blocks is greater than a threshold indicating that the two blocks match each other.

The discriminating of the blocks may include determining that a block in the reference tissue edge image includes the edge of the at least one tissue component if a normalized cross-correlation (NCC) indicating a similarity between the block in the reference tissue edge image and a corresponding block in the first tissue edge image or the second tissue edge image is greater than a threshold indicating that the two blocks include the edge of the at least one tissue component.

The removing of the noise component may include performing a wavelet transformation on the reference ultrasound image to obtain wavelet coefficients respectively corresponding to the pixels of the reference ultrasound image; removing the noise component from the reference ultrasound image by the shrinking the wavelet coefficients respectively corresponding to pixels of the reference ultrasound image that correspond to pixels of the aggregated tissue edge image from which the noise component has been removed based on information about the pixels of the aggregated tissue edge image from which the noise component has been removed; and performing an inverse wavelet transformation on the wavelet coefficients respectively corresponding to the pixels of the reference ultrasound image including the shrunk wavelet coefficients to restore the reference ultrasound image without the noise component.

The wavelet transformation may divide the reference ultrasound image into a plurality of band images in different frequency bands, and may be repeatedly performed with respect to a band image in a low frequency band to divide the reference ultrasound image into a plurality of band images having a plurality of resolution levels; and the inverse wavelet transformation may be performed a same number of times as the wavelet transformation has been repeatedly performed.

The shrinking of the wavelet coefficients may include multiplying each of the wavelet coefficients by a respective edge weight in a range from about 0 to about 1 that is generated based on the aggregated tissue edge image.

The shrinking of the wavelet coefficients may further include multiplying each of the wavelet coefficients multiplied by the respective edge weight by a shrinkage gain function value in a range from about 0 to about 1 that is generated based on the band images generated by the wavelet transformation.

The removing of the noise component may further include performing an edge enhancement to sharpen an outline of the edge of the at least one tissue component in the reference ultrasound image based on information about pixels of the aggregated tissue edge image corresponding to the edge of the at least one tissue component.

The performing of the edge enhancement may include applying an edge enhancement filter to the pixels of the reference ultrasound image, where a weight of the edge enhancement filter applied to pixels of the reference ultrasound image corresponding to the edge of the at least one tissue component is different from a weight of the edge enhancement filter applied to pixels of the reference ultrasound image not corresponding to the edge of the at least one tissue component.

The plurality of 2D ultrasound images may b adjacent to each other in 2D ultrasound images extractable from the 3D ultrasound volume data.

The noise component may include speckle noise generated by an interference phenomenon occurring between ultrasonic wavelengths.

The generating of the plurality of tissue edge images may include generating gradient images in vertical and horizontal directions for each pixel in each of the plurality of 2D ultrasound images; generating a structure matrix for each pixel in each of the plurality of 2D ultrasound images based on the gradient images in the vertical and horizontal directions; calculating eigenvectors having maximum and minimum variations and eigenvalues corresponding to the eigenvectors from the structure matrix; and detecting the edge of the at least one tissue component based on a difference between the eigenvalues.

The detecting of the edge of the at least one tissue component may include detecting the edge of the at least one tissue component when the difference between the eigenvalues is greater than a predetermined value.

In another general aspect, a non-transitory computer-readable storage medium stores a program for controlling a computer to perform the method of claim 1.

In another general aspect, an apparatus for processing an ultrasound image includes an input unit configured to receive three-dimensional (3D) ultrasound volume data of an object to be diagnosed; an image processor configured to generate a plurality of two-dimensional (2D) ultrasound images from the 3D ultrasound volume data, generate a plurality of tissue edge images of an edge of at least one tissue component in the object to be diagnosed based on values of a plurality of pixels forming each of the 2D ultrasound images generated from the 3D ultrasound volume data, and generate a 2D ultrasound image from which a noise component has been removed by discriminating the edge of the at least one tissue component from a position of the noise component based on a difference between a similarity of the edge of the at least one tissue component in the tissue edge images and a similarity of the noise component in the tissue edge images; and an output unit configured to output the 2D ultrasound image from which the noise component has been removed.

The image processor may include a 2D image generator configured to generate the plurality of 2D ultrasound images from the 3D ultrasound volume data; a tissue edge image generator configured to generate the plurality of tissue edge images of the edge of the at least one tissue component in the object to be diagnosed based on the values of the plurality of pixels forming each of the 2D ultrasound images generated from the 3D ultrasound volume data; an aggregated tissue edge image generator configured to identify the edge of the at least one tissue component based on the difference between the similarity of the edge of the at least one tissue component in the tissue edge images and the similarity of the noise component in the tissue edge images and generate, from the tissue edge images, an aggregated tissue edge image from which the noise component has been removed; and an image manipulator configured to remove the noise component from one of the 2D ultrasound images generated from the 3D ultrasound volume data based on the aggregated tissue edge image.

The apparatus may further include a storage unit configured to store all kinds of images generated by the image processor.

Other features and aspects will be apparent from the following detailed description, the drawings, and the claims.

BRIEF DESCRIPTION OF THE DRAWINGS

FIG. 3 is a schematic flowchart illustrating an example of an ultrasound image processing method;

FIG. 4 is a flowchart illustrating an example of a process of generating a single-slice-based tissue edge image corresponding to a single two-dimensional (2D) ultrasound image from the single 2D ultrasound image;

FIGS. 5A and 5B are images illustrating examples of an edge of a tissue component and a non-edge area determined using a structure matrix;

FIG. 6 illustrates an example of an acquired single-slice-based tissue edge image;

FIG. 7 is a flowchart illustrating an example of a process of generating a multi-slice-based aggregated tissue edge image from a plurality of single-slice-based tissue edge images;

FIGS. 8A and 8B are images illustrating examples of blocks including an edge of a tissue component that match with each other in a block matching process for generating an aggregated tissue edge image;

FIGS. 9A and 9B are images illustrating examples of blocks not including an edge of a tissue component that match with each other in the block matching process for generating an aggregated tissue edge image;

DETAILED DESCRIPTION

Figure 1:
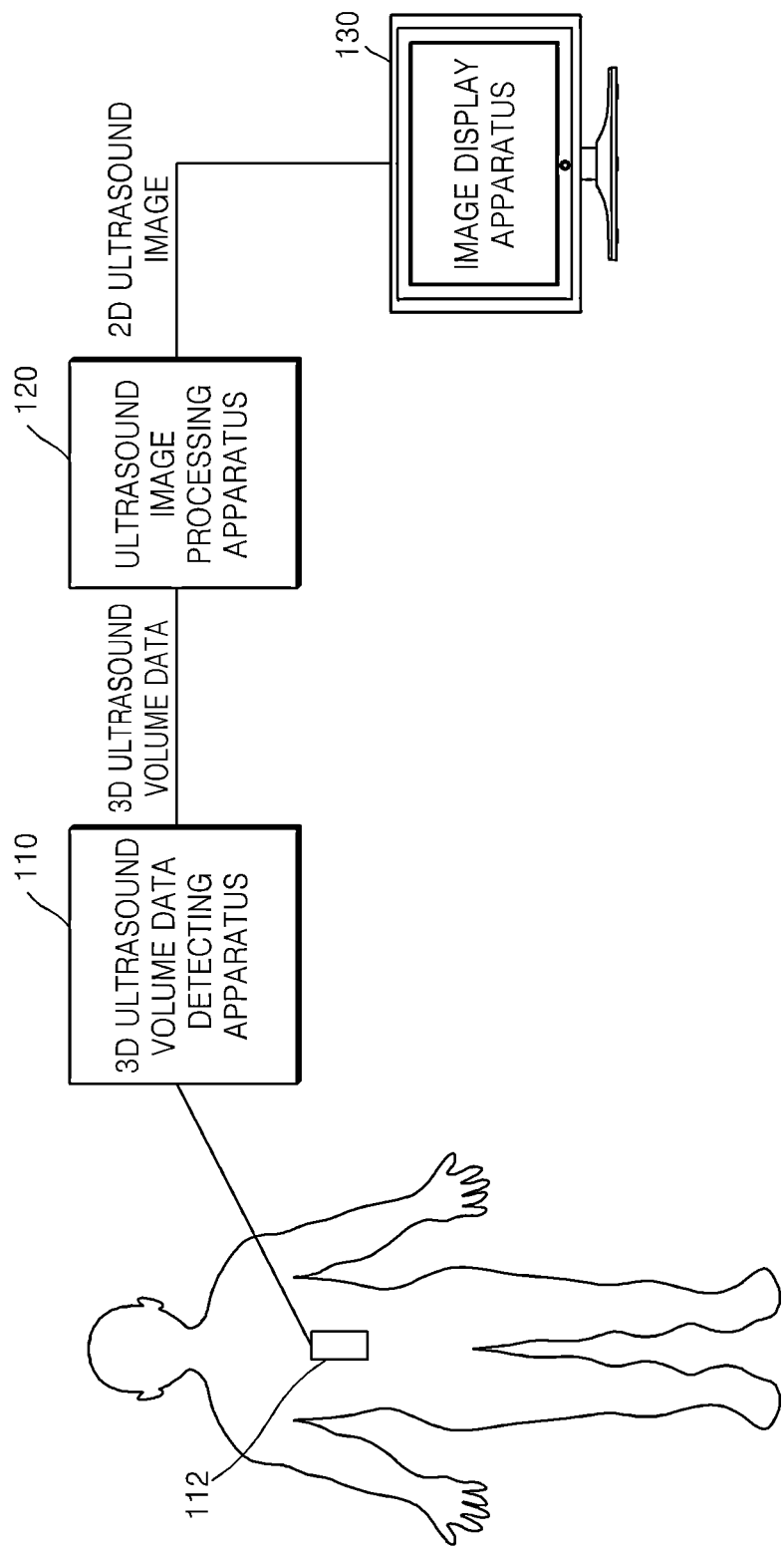
FIG. 1 is a schematic block diagram illustrating an example of an ultrasound diagnosis system.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

FIG. 1 is a schematic block diagram of an example of an ultrasound diagnosis system. Referring to FIG. 1, the ultrasound diagnosis system includes a three-dimensional (3D) ultrasound volume data detecting apparatus 110, an ultrasound image processing apparatus 120, and an image display apparatus 130.

The 3D ultrasound volume data detecting apparatus 110 includes a probe 112. The probe 112 radiates an ultrasound wave as a source signal to a predetermined part of a human body, i.e., an object to be diagnosed, receives ultrasound waves reflected from the object to be diagnosed, and transmits a response signal to the 3D ultrasound volume data detecting apparatus 110. In general, a probe in an ultrasound diagnosis apparatus includes a piezoelectric transducer radiating an ultrasound wave in a range from about 2 MHz to about 18 MHz to an object to be diagnosed. The ultrasound wave is reflected back to the probe from various tissues in the object to be diagnosed, and the reflected ultrasound waves vibrate the piezoelectric transducer to generate a response signal of electric pulses. The 3D ultrasound volume data detecting apparatus 110 generates 3D ultrasound volume data by using the response signal received from the probe 112.

Examples of generating 3D ultrasound volume data in the 3D ultrasound volume data detecting apparatus 110 are as follows. The 3D ultrasound volume data detecting apparatus 110 may generate 3D ultrasound volume data for three-dimensionally showing an object to be diagnosed by detecting a plurality of pieces of cross-sectional ultrasound data while changing a position and direction of the probe 112 and accumulating the plurality of pieces of cross-sectional ultrasound data. Alternatively, the 3D ultrasound volume data detecting apparatus 110 may generate 3D ultrasound volume data by detecting a plurality of pieces of cross-sectional ultrasound data by using a plurality of probes 112 and accumulating the plurality of pieces of cross-sectional ultrasound data. The generated 3D ultrasound volume data is transmitted to the ultrasound image processing apparatus 120.

The ultrasound image processing apparatus 120 generates a two-dimensional (2D) ultrasound image from the 3D ultrasound volume data received from the 3D ultrasound volume data detecting apparatus 110. Although the ultrasound image processing apparatus 120 may generate a 3D ultrasound image by using the 3D ultrasound volume data, in this example, the ultrasound image processing apparatus 120 generates a 2D ultrasound image because visibility of tissues in the object to be diagnosed decreases due to overlap of images, medical experts are familiar with dealing with 2D images, and the image display apparatus 130 generally displays 2D images.

A large number of 2D images may be generated from 3D volume data. Cross-sections in various directions crossing 3D ultrasound volume data may be considered, wherein a 2D ultrasound image may be generated by ultrasound data corresponding to each cross-section. By crossing a 3D volume at a predetermined spacing in the same direction, a plurality of 2D images parallel to each other may be generated. The generated 2D ultrasound image is transmitted to the image display apparatus 130, and the image display apparatus 130 displays the generated 2D ultrasound image.

Figure 2:
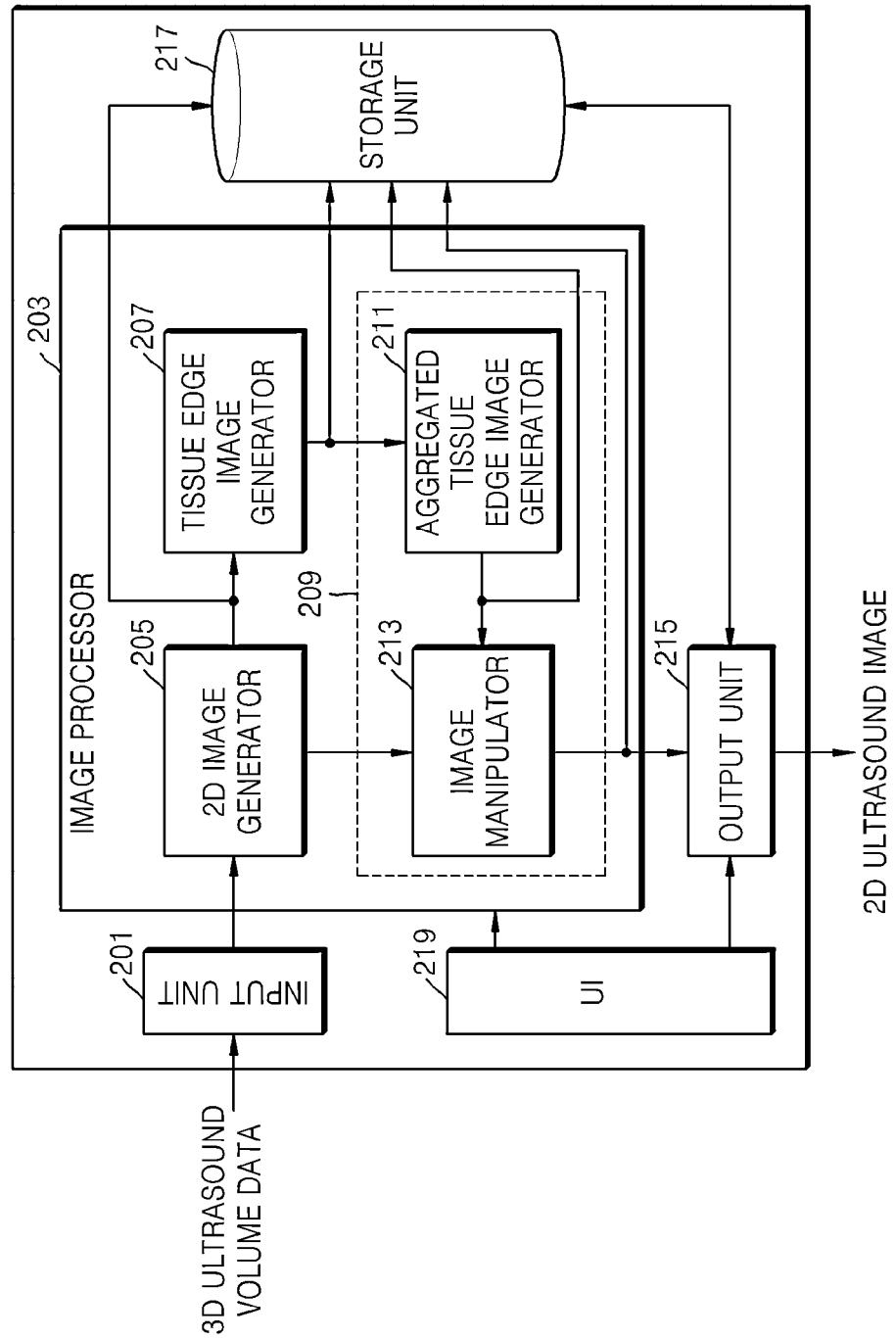
FIG. 2 is a block diagram illustrating an example of an ultrasound image processing apparatus of FIG. 1.

FIG. 2 is a block diagram illustrating an example of the ultrasound image processing apparatus 120 of FIG. 1. Referring to FIG. 2, the ultrasound image processing apparatus 120 includes an input unit 201, an image processor 203, an output unit 215, a storage unit 217, and a user interface (UI) 219.

The input unit 201 receives 3D ultrasound volume data of an object to be diagnosed from the 3D ultrasound volume data detecting apparatus 110 and transmits the 3D ultrasound volume data to the image processor 203. The output unit 215 receives a 2D ultrasound image from the image processor 203 and transmits the 2D ultrasound image to the image display apparatus 130. That is, the input unit 201 and the output unit 215 are interfaces for connecting the image processor 203 of the ultrasound image processing apparatus 120 to the 3D ultrasound volume data detecting apparatus 110 and the image display apparatus 130 outside the ultrasound image processing apparatus 120. The UI 219 is an interface for a user such as a medical expert to input a command, and may be implemented in various ways, such as by using a keyboard, a mouse, a touch panel, and any other user input device known to one of ordinary skill in the art.

The image processor 203 generates a plurality of 2D ultrasound images crossing a 3D volume after receiving the 3D ultrasound volume data from the input unit 201, and generates a 2D ultrasound image having an enhanced image quality by performing image processing, such as removing noise from each of the generated 2D ultrasound images. In the example in FIG. 2, the image processor 203 includes a 2D image generator 205, a tissue edge image generator 207, and an image quality enhancement processor 209, and the image quality enhancement processor 209 includes an aggregated tissue edge image generator 211 and an image manipulator 213.

The 2D image generator 205 generates a plurality of 2D ultrasound images by using the 3D ultrasound volume data. The 2D image generator 205 generates a 2D ultrasound image by extracting ultrasound data corresponding to a cross section crossing a 3D ultrasound volume. The 2D image generator 205 may generate a large number of 2D ultrasound images according to a crossing direction, including 2D ultrasound images parallel to each other. For example, considering rectangular coordinates consisting of X, Y, and Z axes, 2D X-Y plane images perpendicular to the Z axis may be generated while changing only a Z value by a predetermined spacing. The 2D ultrasound images may be considered to be a reference ultrasound image and a plurality of neighboring ultrasound images. The reference ultrasound image may be an ultrasound image corresponding to an intermediate position among the 2D ultrasound images.

For example, in an example in which there are a total of three ultrasound images, i.e., (N−1)th, Nth, and (N+1)th ultrasound images, the Nth ultrasound image may be the reference ultrasound image. If N=2, there are first to third ultrasound images, and the second ultrasound image corresponding to an intermediate position is the reference ultrasound image. The reference ultrasound image is used as an ultrasound image to finally enhance image quality. Hereinafter, for convenience of description, an example in which a total of three ultrasound images, i.e., (N−1)th, Nth, and (N+1) th ultrasound images, are generated and the Nth ultrasound image is the reference ultrasound image will be described. Of course, although three ultrasound images are generated in the following example, this is only an example, and more than three ultrasound images may be generated. When more than three 2D ultrasound images are generated, some of the 2D ultrasound images may be selected and used in the following example. Alternatively, some of a plurality of 2D ultrasound images may be sequentially used in the following example while changing a reference ultrasound image. For example, when a total of five ultrasound images, i.e., 1st, 2nd, 3rd, 4th, 5th ultrasound images, are used, three sets of ultrasound images, i.e., (1,2,3), (2,3,4), (3,4,5), may be sequentially acquired and 2nd, 3rd, 4th ultrasound images may be the reference ultrasound image in each of the sets.

The tissue edge image generator 207 receives the plurality of 2D ultrasound images from the 2D image generator 205 and generates tissue edge images respectively corresponding to the 2D ultrasound images from the 2D ultrasound images. A tissue edge image is an image of a boundary between a tissue component of an object to be diagnosed with an ultrasound wave, i.e., an organ inside a human body, and other parts. This boundary is an edge of the tissue component, or a tissue edge. Since a tissue edge in an ultrasound image contains medically significant information, information regarding the tissue edge in the ultrasound image is preserved. The tissue edge image generator 207 generates a tissue edge image by identifying whether a position of each pixel in an ultrasound image corresponds to an edge of the tissue component based on pixel value information of a plurality of pixels forming the 2D ultrasound image. By doing this, the tissue edge image generator 207 generates the plurality of tissue edge images respectively corresponding to the 2D ultrasound images. A tissue edge image corresponding to the reference ultrasound image, i.e., the second ultrasound image of the three ultrasound images in this example, is a reference tissue edge image. The tissue edge image generator 207 transmits the plurality of generated tissue edge images to the aggregated tissue edge image generator 211.

The aggregated tissue edge image generator 211 receives the plurality of tissue edge images from the tissue edge image generator 207 and generates an aggregated tissue edge image from the plurality of tissue edge images. The aggregated tissue edge image is an image obtained by removing noise from the reference tissue edge image corresponding to the reference ultrasound image by discriminating the edge of the tissue component from a position of noise by comparing the reference tissue edge image with the neighboring tissue edge images. The aggregated tissue edge image is used as a reference image to perceive the edge of the tissue component by comparing the reference tissue edge image with the neighboring tissue edge images and to correctly perceive the edge of the tissue component in an ultrasound image by removing noise that makes perceiving the edge of the tissue component difficult. The perceiving of the edge of the tissue component by using the tissue edge images is achieved based on physical characteristics of the edge of the tissue component and noise.

In greater detail, the fact that a similarity of the edge of the tissue component existing throughout the neighboring tissue edge images differs from a similarity of noise components is used. The aggregated tissue edge image generator 211 transmits the generated aggregated tissue edge image to the image manipulator 213.

The image manipulator 213 receives the aggregated tissue edge image from the aggregated tissue edge image generator 211 and generates an image-quality-enhanced 2D ultrasound image by removing noise from a 2D ultrasound image by using the aggregated tissue edge image. The 2D ultrasound image from which noise is removed is the reference ultrasound image because the aggregated tissue edge image is generated by comparing the reference tissue edge image with the neighboring tissue edge images, wherein the reference tissue edge image is a tissue edge image corresponding to the reference ultrasound image. The aggregated tissue edge image is used to perceive a position of a part corresponding to the edge of the tissue component in a 2D ultrasound image and perform predetermined processing on the edge of the tissue component and noise. The image manipulator 213 may also sharpen an outline of a part corresponding to the edge of the tissue component by using an edge enhancement process to produce a high-definition ultrasound image whose image quality has been finally enhanced. The 2D ultrasound image from which noise has been removed using the aggregated tissue edge image is transmitted to the output unit 215.

The storage unit 217 stores all of the different kinds of images generated in the image processor 203. That is, the storage unit 217 stores the 2D ultrasound images generated by the 2D image generator 205, the tissue edge images generated by the tissue edge image generator 207, the aggregated tissue edge image generated by the aggregated tissue edge image generator 211, and the image-quality-enhanced 2D ultrasound image generated by the image manipulator 213. The storage unit 217 transmits the stored images to the output unit 215 according to a request of a user.

FIG. 3 is a schematic flowchart illustrating an example of an ultrasound image processing method. Although omitted below, the above description of the ultrasound image processing apparatus 120 shown in FIG. 2 also applies to the ultrasound image processing method shown in FIG. 3.

Referring to FIG. 3, in operation 301, the 2D image generator 205 generates a plurality of 2D ultrasound images from 3D ultrasound volume data. The plurality of 2D ultrasound images used in this example may be obtained by extracting a plurality of 2D ultrasound images crossing a 3D volume from the 3D ultrasound volume data, the plurality of 2D ultrasound images being parallel to each other and having a predetermined spacing therebetween. The predetermined spacing may be changed to a proper value according to each case, i.e., by considering a time taken for ultrasound image processing and an image quality of an ultrasound image. The smaller the predetermined spacing is, the less an image change between neighboring 2D ultrasound images will be. At least two or more of the plurality of 2D ultrasound images may be selected and used.

In operation 303, the tissue edge image generator 207 generates a plurality of tissue edge images respectively corresponding to the plurality of 2D ultrasound images. Each 2D ultrasound image is formed by a plurality of pixels, and an edge of a tissue component in the 2D ultrasound image is detected by using each pixel value. When three ultrasound images are used, three corresponding tissue edge images are generated.

In operation 305, the aggregated tissue edge image generator 211 generates an aggregated tissue edge image from the plurality of tissue edge images. As described above, the aggregated tissue edge image is an image obtained by removing noise from a reference tissue edge image corresponding to a reference ultrasound image by discriminating the edge of the tissue component from a position of noise by comparing the reference tissue edge image with neighboring tissue edge images. The removing of the noise may be achieved by identifying a noise component based on physical characteristics of the edge of the tissue component and the noise and performing a noise removing process, such as filtering, for only a part determined to be the noise component to leave only the edge of the tissue component. The aggregated tissue edge image is used to enhance image quality of a 2D ultrasound image.

In operation 307, the image manipulator 213 acquires an image-quality-enhanced 2D ultrasound image by using the aggregated tissue edge image. A boundary between tissues may be correctly identified by using the aggregated tissue edge image, and the noise removing process is performed for noise except for the edge of the tissue component in the reference ultrasound image based on the boundary between tissues. In addition, by sharpening an outline of a part corresponding to the edge of the tissue component by using an edge enhancement process, a high-definition ultrasound image whose image quality has been finally enhanced may be acquired.

The operations described above will be described in greater detail below.

FIG. 4 is a flowchart illustrating an example of a process of generating a single-slice-based tissue edge image corresponding to a single 2D ultrasound image from the single 2D ultrasound image. The term "single-slice-based" indicates that a plurality of tissue edge images respectively corresponding to a plurality of 2D ultrasound images are generated from individual ones of the plurality of 2D ultrasound images. That is, each tissue edge image is generated based only on a corresponding 2D ultrasound image. To generate a tissue edge image corresponding to each of the plurality of 2D ultrasound images acquired by data-processing 3D volume data, the following tissue edge image acquiring process is performed. FIG. 4 is a detailed flowchart corresponding to operation 303 of FIG. 3.

Referring to FIG. 4, in operation 401, the tissue edge image generator 207 acquires one of a plurality of 2D ultrasound images. An order of selecting and acquiring the one of the plurality of 2D ultrasound images is not significant. Since the process of FIG. 4 may be performed sequentially beginning with an arbitrary ultrasound image or simultaneously for all ultrasound images with respect to the plurality of 2D ultrasound images, operation 401 may also be performed sequentially beginning with an arbitrary ultrasound image or simultaneously for all ultrasound images with respect to the plurality of 2D ultrasound images. For example, when a total of three ultrasound images, i.e., (N−1)th, Nth, and (N+1)th ultrasound images, are used, ultrasound images may be sequentially acquired by sequentially selecting the (N−1)th ultrasound image, the Nth ultrasound image, and the (N+1)th ultrasound image, or the following process may be simultaneously performed by simultaneously selecting all of the (N−1)th, Nth, and (N+1)th ultrasound images.

In operation 403, the tissue edge image generator 207 removes an initial noise component from each ultrasound image. A Gaussian low-pass filter (LPF) or any other type of LPF known to one of ordinary skill in the art may be used to remove the initial noise component.

In operation 405, the tissue edge image generator 207 generates vertical and horizontal gradient images with respect to each pixel in the ultrasound image. That is, for a pixel value at a position (x,y) in the ultrasound image on coordinates consisting of the X axis and the Y axis, degrees of variation of the pixel value in the vertical and horizontal directions are obtained. Vertical and horizontal gradients of a pixel value I may be obtained using the following Equation 1:

$$\nabla I = \begin{pmatrix} \frac{\partial I}{\partial x} \\ \frac{\partial I}{\partial y} \end{pmatrix} = \begin{pmatrix} I_x \\ I_y \end{pmatrix} \quad (1)$$

In Equation 1, $I_x$ denotes a horizontal gradient value, and $I_y$ denotes a vertical gradient value.

In operation 407, the tissue edge image generator 207 generates a structure matrix by using the vertical and horizontal gradient values $I_x$ and $I_y$ of the pixel value I that are obtained in operation 405. The structure matrix may be generated using the following Equation 2:

$$\text{Structure Matrix} = \begin{bmatrix} I_x^2 & I_x I_y \\ I_x I_y & I_y^2 \end{bmatrix} \quad (2)$$

To minimize the influence of speckle noise, the structure matrix of Equation 2 may be converted to a structure matrix of Equation 3 by applying a Gaussian convolution kernel.

$$J_\rho(I) = \begin{bmatrix} K_\rho * I_x^2 & K_\rho * (I_x I_y) \\ K_\rho * (I_x I_y) & K_\rho * I_y^2 \end{bmatrix} \quad (3)$$

In Equation 3, * denotes a convolution operation, and $K_\rho$ denotes a Gaussian convolution kernel (ρ denotes a variance of Gaussian convolution kernel) represented by the following Equation 4:

$$K_\rho(x, y) = (2\pi\rho^2)^{-1}\left(\frac{x^2 + y^2}{2\rho^2}\right) \quad (4)$$

In operation 409, eigenvalue decomposition is performed on the structure matrix of Equation 3. A result of the eigenvalue decomposition is expressed by the following Equation 5:

$$J(I) = [w_1 \ w_2]\begin{bmatrix} \mu_1 & 0 \\ 0 & \mu_2 \end{bmatrix}\begin{bmatrix} w_1^T \\ w_2^T \end{bmatrix} \quad (5)$$

In Equation 5, $w_1$ and $w_2$ denote eigenvectors, and $\mu_1$ and $\mu_2$ denote eigenvalues. The eigenvector $w_1$ is a vector indicating a direction in which a gradient varies most quickly, and indicates a direction perpendicular to a predetermined structure. The eigenvector $w_2$ is a vector indicating a direction perpendicular to the eigenvector $w_1$. That is, the eigenvectors $w_1$ and $w_2$ denote eigenvectors in directions having the maximum and minimum variations, respectively. The eigenvalues $\mu_1$ and $\mu_2$ are scalar values indicating the magnitudes, i.e., gradients, of the eigenvectors $w_1$ and $w_2$, respectively. In other words, the eigenvalues $\mu_1$ and $\mu_2$ denote gradients in the directions having the maximum and minimum variations, respectively.

In operation 411, the tissue edge image generator 207 selects eigenvectors in directions having the maximum and minimum variations.

In operation 413, the tissue edge image generator 207 obtains eigenvalues of the selected eigenvectors and calculates a difference between the eigenvalues. The difference between the eigenvalues is a significant reference value for detecting an edge of a tissue component and a noise or homogeneous area because an eigenvalue difference between an eigenvector following an edge of the tissue component and an eigenvector perpendicular thereto is large in the edge of the tissue component, while an eigenvalue difference between perpendicular eigenvectors is small in the noise or homogeneous area due to there being no edge information of the tissue component.

In other words, a large difference between two eigenvalues indicates a large gradient in one direction, and thus it is determined that a corresponding pixel corresponds to an edge of a tissue component in an object to be diagnosed. On the contrary, a small difference between two eigenvalues indicates no directivity in any direction, because noise has large gradient values in both directions and a homogeneous area (irrelevant to an edge of a tissue component) has small gradient values in both directions, and therefore a difference between the two gradient values, i.e., an eigenvalue difference, is small, and thus it is determined that a corresponding pixel does not correspond to the edge of the tissue component in the object to be diagnosed. Whether each pixel corresponds to the edge of the tissue component in the object to be diagnosed is determined by defining a predetermined value and comparing a difference between two eigenvalues with the predetermined value.

In operation 415, if the difference between the eigenvalues is greater than the predetermined value, the tissue edge image generator 207 proceeds to operation 417. Otherwise, if the difference between the eigenvalues is equal to or less than the predetermined value, the tissue edge image generator 207 proceeds to operation 419.

In operation 417, the tissue edge image generator 207 determines that a corresponding pixel corresponds to an edge of a tissue component because the difference between the eigenvalues is greater than the predetermined value, and a large variation of a pixel value in a predetermined direction may be considered to indicate an edge of a tissue component in an object to be diagnosed.

In operation 419, the tissue edge image generator 207 determines that a corresponding pixel does not correspond to an edge of a tissue component in an object to be diagnosed because the difference between the eigenvalues is equal to or less than the predetermined and a small eigenvalue difference indicates large or small gradients in both directions, indicating noise or a homogeneous area instead of an edge of a tissue component.

In operation 421, the tissue edge image generator 207 determines whether the determination of whether a pixel corresponds to an edge of the tissue component has been performed for all pixels in the ultrasound image. If it has, the tissue edge image generator 207 ends the process. Otherwise, if it has not, the tissue edge image generator 207 proceeds to operation 407 to repeat the operations 407 to 419 for the remaining pixels. Alternatively, operations 407 to 419 may be simultaneously performed for all pixels.

FIGS. 5A and 5B are images illustrating examples of an edge of a tissue component and a non-edge area determined using a structure matrix. FIG. 5A shows an edge of a tissue component that is represented by two arrows having different lengths perpendicular to each other to indicate that an eigenvalue difference between an eigenvector perpendicular to the edge of the tissue component and an eigenvector parallel to the edge of the tissue component is large in the edge of the tissue component. On the contrary, FIG. 5B shows a non-edge area that is represented by two arrows having almost the same length perpendicular to each other to indicate that eigenvalues of two eigenvectors perpendicular to each other are almost the same in the non-edge area because there is no information regarding an edge of the tissue component, resulting in a small eigenvalue difference.

FIG. 6 illustrates an example of an acquired single-slice-based tissue edge image. Referring to FIG. 6, a part determined as an edge of a tissue component has a bright color, and a dark area, i.e., a non-edge area, corresponds to a homogeneous area in which there is no object to be diagnosed. In the dark area, speckle patterns having a bright color appear. These speckle patterns are noise. Image quality is degraded by the speckle noise, causing the edge of the tissue component to be incorrectly identified. As described above, because the single-slice-based tissue edge image includes a lot of noise, it is difficult to correctly identify the edge of the tissue component, and thus a new tissue edge image in which noise has been reduced is necessary. A process of generating a new tissue edge image in which noise has been reduced will be described below.

FIG. 7 is a flowchart illustrating an example of a process of generating a multi-slice-based aggregated tissue edge image from a plurality of single-slice-based tissue edge images. FIG. 7 is a detailed flowchart corresponding to operation 305 of FIG. 3.

Referring to FIG. 7, in operation 701, the aggregated tissue edge image generator 211 acquires a plurality of tissue edge images. As described above, a plurality of tissue edge images respectively corresponding to a plurality of ultrasound images may be acquired. A tissue edge image corresponding to a reference ultrasound image is called a reference tissue edge image. When a total of three ultrasound images, i.e., (N−1)th, Nth, and (N+1)th ultrasound images, are used, a total of three tissue edge images, i.e., (N−1)th, Nth, and (N+1)th tissue edge images, respectively corresponding to the (N−1)th, Nth, and (N+1)th ultrasound images are acquired, wherein the Nth tissue edge image is the reference tissue edge image. This premise will be applied in the following description. Since the plurality of tissue edge images are generated from neighboring ultrasound images, the plurality of tissue edge images are also adjacent to each other.

In operation 703, the aggregated tissue edge image generator 211 divides each of the adjacent tissue edge images into block images having a predetermined size and detects blocks matching with each other by block matching. Each of the tissue edge images may be divided into a plurality of blocks having the same size. In this case, similar blocks may be matched with each other by determining a similarity between blocks. In greater detail, similar blocks matching with each other are detected by determining a similarity between corresponding blocks having a predetermined size in the (N−1)th tissue edge image and the Nth reference tissue edge image. Thereafter, similar blocks matching with each other are detected by determining a similarity between corresponding blocks having the predetermined size in the Nth reference tissue edge image and the (N+1)th tissue edge image. Since the size of the blocks is the same in every tissue edge image, and is small, the determination of the similarity may be correctly performed. A block in the Nth reference tissue edge image is called a reference block.

To detect similar blocks by block matching, normalized cross-correlation (NCC) may be used. If an NCC value is large, a similarity between two images is also large. If the NCC is greater than a first threshold that is a criterion for determining whether two blocks match with each other, the two blocks are determined to match with each other. The NCC may be obtained using the following Equation 6:

$$NCC = \frac{1}{n-1} \sum_{x,y} \frac{(f(x,y) - \bar{f})(t(x,y) - \bar{t})}{\sigma_f \sigma_t} \quad (6)$$

In Equation 6, n denotes the number of pixels in a block, (x,y) denotes coordinates of a pixel in the block, f(x,y) denotes a pixel value of a reference block, $\bar{f}$ denotes a mean pixel value of the reference block, t(x,y) denotes a pixel value of a target block, $\bar{t}$ denotes a mean pixel value of the target block, $\sigma_f$ denotes a standard deviation of pixel values of the reference block, and $\sigma_t$ denotes a standard deviation of pixel values of the target block.

The physical meaning of the NCC is as follows. When all pixels in a single image are arranged in a row, a single vector may be obtained. It is assumed that F(x,y) and T(x,y) are image vectors generated by the following Equation 7:

$$F(x,y)=f(x,y)-\bar{f}, T(x,y)=t(x,y)-\bar{t} \quad (7)$$

In this case, because an inner product $\langle F,T \rangle$ of F and T is $|F||T|\cos\theta$, a cosine value obtained from the two vectors may be calculated by the following Equation 8, and the NCC of Equation 6 is equal to Equation 8.

$$\left\langle \frac{F}{\|F\|}, \frac{T}{\|T\|} \right\rangle \quad (8)$$

In Equation 8, $\|\cdot\|$ is the $L^2$ norm. That is, the physical meaning of the NCC is a cosine value of an angle between two vectors corresponding to two images.

In operation 705, the aggregated tissue edge image generator 211 performs three-dimensional block decomposition with respect to the blocks matching with each other. That is, blocks including an edge of a tissue component and blocks not including an edge of a tissue component are discriminated from each other and detected from among adjacent blocks matching with each other based on an image variation between adjacent blocks about the reference block in the reference tissue edge image. In general, the edge of the tissue component continuously appears on adjacent images, and accordingly, parts corresponding to the edge of the tissue component in the adjacent images will be almost the same. Thus, the adjacent blocks including the edge of the tissue component are very similar. On the contrary, because a noise component appears at different positions even on adjacent images, most parts corresponding to the noise component in the adjacent images do not continuously appear. Thus, a block including only a noise component without an edge of a tissue component is different from a matching block in a next adjacent image. In other words, similarity between blocks including an edge of a tissue component is high, while similarity between blocks not including an edge of a tissue component is low.

For example, when the Nth reference block includes an edge of a tissue component that has a bright color, the possibility that the edge of the tissue component that has a bright color continuously exists at a position in a next adjacent block that corresponds to a position of the edge of the tissue component in the Nth reference block is high. That is, the edge of the tissue component is continuously represented without suddenly disappearing in a next image and has only a minute difference, so parts corresponding to the edge of the tissue component in adjacent images have a high similarity. On the contrary, when the Nth reference block includes speckle noise without an edge of a tissue component, the possibility that noise does not exist at a position in an adjacent image that corresponds to a predetermined noise position in the Nth reference block is high, and noise appears at different positions, so there is no continuity. Thus, block images including noise without an edge of a tissue component have different image information even though they are adjacent images. That is, a part shown as a bright speckle (noise) in a reference block may be shown as dark at a corresponding position in a next adjacent block, or a part shown as dark in the reference block may be shown as a bright speckle at a corresponding position in the next adjacent block.

In this case, the NCC that has been used for matching between blocks may be used to discriminate a block including an edge of a tissue component from a block not including an edge of a tissue component. Whether a block includes an edge of a tissue component may be determined by using a second threshold that is different from the first threshold for matching between blocks. For example, if it is assumed that the first threshold for the block matching is 0.7 and the second threshold for determining whether a block includes an edge of a tissue component is 0.9, when an NCC between a reference block and an adjacent block is less than 0.7, it may be determined that the reference block and the adjacent block do not match with each other, when the NCC is equal to or greater than 0.7 and less than 0.9, it may be determined that the reference block and the adjacent block match with each other without including an edge of a tissue component, and when the NCC is equal to or greater than 0.9, it may be determined that the reference block and the adjacent block match with each other and include an edge of a tissue component.

FIGS. 8A and 8B are images illustrating examples of blocks including an edge of a tissue component that match with each other in a block matching process for generating an aggregated tissue edge image. FIG. 8A shows a block corresponding to a portion of an (N−1)th tissue edge image, and FIG. 8B shows a reference block corresponding to a portion of an Nth reference tissue edge image. The two blocks match with each other, and bright parts in the two blocks correspond to the edge of the tissue component. That is, image information of blocks including the edge of the tissue component is almost the same. Since blocks matching with each other are adjacent to each other and an edge of a tissue component does not suddenly disappear in a next image, the edge of the tissue component in a block also appears in a corresponding block of an adjacent tissue edge image. As a result, a block including a part corresponding to an edge of a tissue component has an image quite similar to an image of an adjacent matching block.

FIGS. 9A and 9B are images illustrating examples of blocks not including an edge of a tissue component that match with each other in the block matching process for generating an aggregated tissue edge image. FIG. 9A shows a block corresponding to a portion of an (N−1)th tissue edge image, and FIG. 9B shows a reference block corresponding to a portion of an Nth reference tissue edge image. The two blocks match with each other and include noise instead of a part corresponding to the edge of the tissue component, so image information of the two blocks is different from each other. Generally, noise does not continuously appear at corresponding positions of matching blocks adjacent to each other. That is, because noise is very unstable, noise does not continuously appear in tissue edge images adjacent to each other, and accordingly, when matching blocks adjacent to each other have noise, image information of the matching blocks will be different from each other.

In operation 707, the aggregated tissue edge image generator 211 performs a filtering process for removing a noise component from reference blocks not including an edge of a tissue component. In the operations described above, whether a reference block includes an edge of a tissue component is determined using the physical characteristics, such as a similarity of an edge of a tissue component and a variation of noise, with respect to adjacent blocks matching with each other. In the current operation, the filtering process for removing the noise component is not performed for blocks including the edge of the tissue component, or is performed for only a portion of the blocks including the edge of the tissue component that is far from the edge of the tissue component, and the filtering process for removing the noise component is performed for blocks not including the edge of the tissue component.

In operation 709, the aggregated tissue edge image generator 211 generates an aggregated tissue edge image by aggregating the reference blocks including the edge of the tissue component and the reference blocks not including the edge of the tissue component on which the filtering process for removing the noise component has been performed. That is, a single tissue edge image is generated by aggregating the reference blocks including the edge of the tissue component and the reference blocks on which the filtering process for removing the noise component has been performed. Since this tissue edge image is generated using a plurality of tissue edge images, the tissue edge image is a multi-slice-based tissue edge image and is called an aggregated tissue edge image. The aggregated tissue edge image is an image in which noise is greatly reduced compared to a single-slice-based tissue edge image because the filtering process for removing the noise component has been performed on all of the aggregated tissue edge image except for the edge of the tissue component. The aggregated tissue edge image is used to remove noise in a reference ultrasound image.

Figure 10:
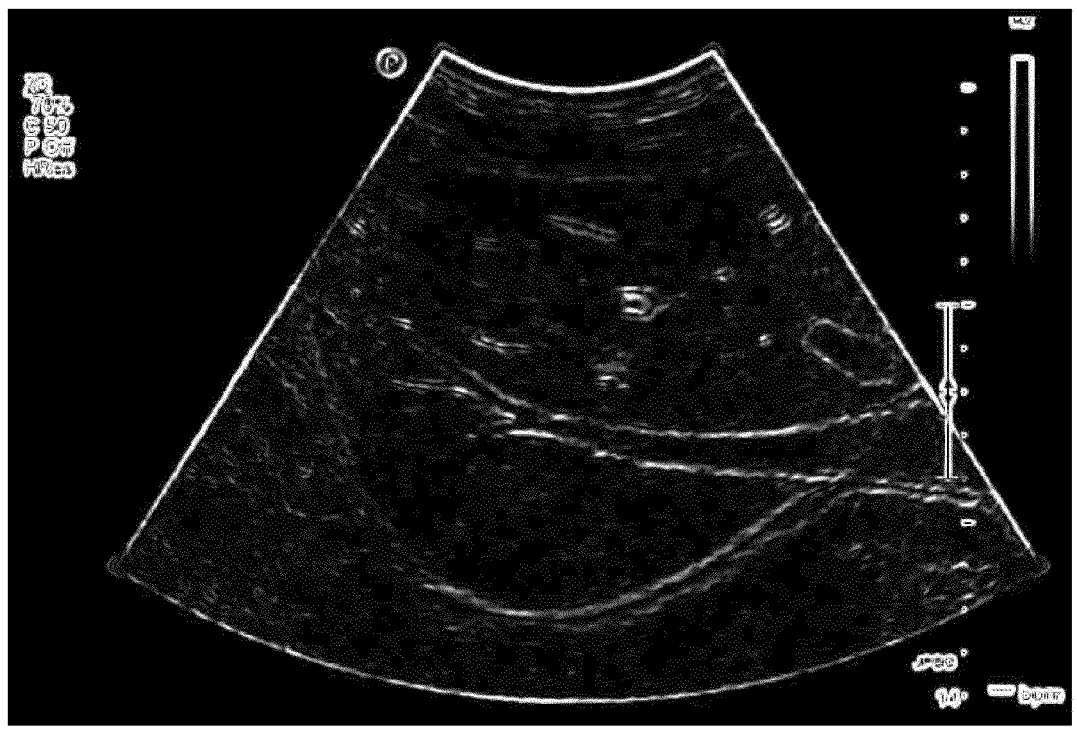
FIG. 10 illustrates an example of an acquired multi-slice-based aggregated tissue edge image.

FIG. 10 illustrates an example of an acquired multi-slice-based aggregated tissue edge image. Compared with the single-slice-based tissue edge image shown in FIG. 6, noise represented as bright speckles is remarkably reduced.

Figure 11:
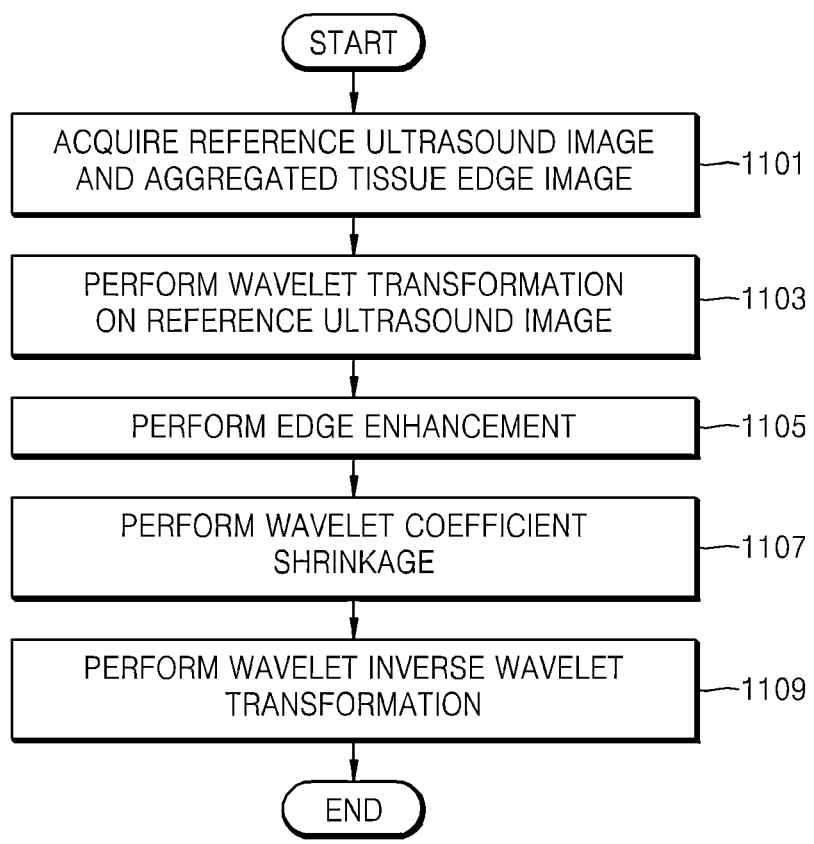
FIG. 11 is a flowchart illustrating an example of a process of acquiring an ultrasound image having an image quality that has been enhanced using an aggregated tissue edge image.

FIG. 11 is a flowchart illustrating an example of a process of acquiring an ultrasound image having an image quality that has been enhanced using an aggregated tissue edge image. FIG. 11 is a detailed flowchart corresponding to operation 307 of FIG. 3. Although various methods may be used to enhance image quality, the following example is based on a method using wavelet transformation.

Referring to FIG. 11, in operation 1101, the image manipulator 213 acquires a reference ultrasound image and an aggregated tissue edge image. The reference ultrasound image is an original ultrasound image including noise and is an ultrasound image from which the noise will be removed using the aggregated tissue edge image. Since the aggregated tissue edge image is generated by comparing the reference tissue edge image corresponding to the reference ultrasound image with adjacent tissue edge images, the aggregated tissue edge image basically corresponds to the reference ultrasound image. Thus, the original ultrasound image from which a noise component will be removed using the aggregated tissue edge image may be the reference ultrasound image.

In operation 1103, the image manipulator 213 performs a wavelet transformation on the reference ultrasound image. The wavelet transformation is a process of dividing a given image signal into several signals of different frequency bands by using two or more filters. The wavelet transformation of a 2D image performs frequency division in horizontal and vertical directions, wherein the frequency division may be performed by passing an image signal through a high frequency filter or a low frequency filter. When the wavelet transformation is performed for an ultrasound image, the ultrasound image is divided into images of 4 bands LL, HL, LH, and HH, wherein L denotes a low frequency component and H denotes a high frequency component. For example, LL indicates that image signals in both the horizontal and vertical directions pass through the low frequency filter, HL indicates that an image signal in the horizontal direction passes through the high frequency filter and an image signal in the vertical direction passes through the low frequency filter, LH indicates that an image signal in the horizontal direction passes through the low frequency filter and an image signal in the vertical direction passes through the high frequency filter, and HH indicates that image signals in both the horizontal and vertical directions pass through the high frequency filter. An image corresponding to an LL band is closest to the original image.

The division by the wavelet transformation may be performed several times, wherein the wavelet transformation is performed for images of the LL band closest to the original image. A level 1 indicates that the wavelet transformation has been performed once, and a level 2 indicates that the wavelet transformation has been performed twice. That is, a level n indicates that the wavelet transformation has been performed n times. Each band is formed by wavelet coefficients corresponding to respective pixels, wherein the wavelet coefficients are obtained by the wavelet transformation.

When the wavelet transformation is performed once for the reference ultrasound image, the reference ultrasound image is divided into images of the 4 bands LL, HL, LH, and HH in the level 1. When the wavelet transformation is performed again for the image of the band LL in the level 1, the image of the band LL in the level 1 is divided into 4 images of the 4 bands LL, HL, LH, and HH in the level 2. At this time, a median per band per level may be calculated. A shrinkage gain function may be generated per band per level by using the calculated median. The shrinkage gain function may be used for wavelet coefficient shrinkage together with an edge weight function obtained using the aggregated tissue edge image and is used to remove noise. However, because the wavelet coefficient shrinkage may be performed using only the edge weight function, the use of the shrinkage gain function is optional. The shrinkage gain function is calculated using the following Equation 9:

$$G_T^{Basic}(W_m) = \max\left\{0, 1 - \frac{M_l^b}{W_m + \varepsilon}\right\} \quad (9)$$

In Equation 9, $W_m$ denotes a mean value of an N×N-sized window including a current pixel, $M_l^b$ denotes a median of pixel values, i.e., wavelet coefficients, in a band b in a level l, and $\varepsilon$ denotes the minimum value of pixel values. The shrinkage gain function of Equation 9 may be expressed by the following Equation 10 to make the shrinkage gain function value smaller or larger.

$$G_T(W_m) = \begin{cases} \frac{1}{2}(2G_T^{Basic})^\alpha, & G_T^{Basic} \leq \frac{1}{2} \\ 1 - \frac{1}{2}(2(1 - G_T^{Basic}))^\alpha, & G_T^{Basic} > \frac{1}{2} \end{cases} \quad (10)$$

Figures 12, 13:
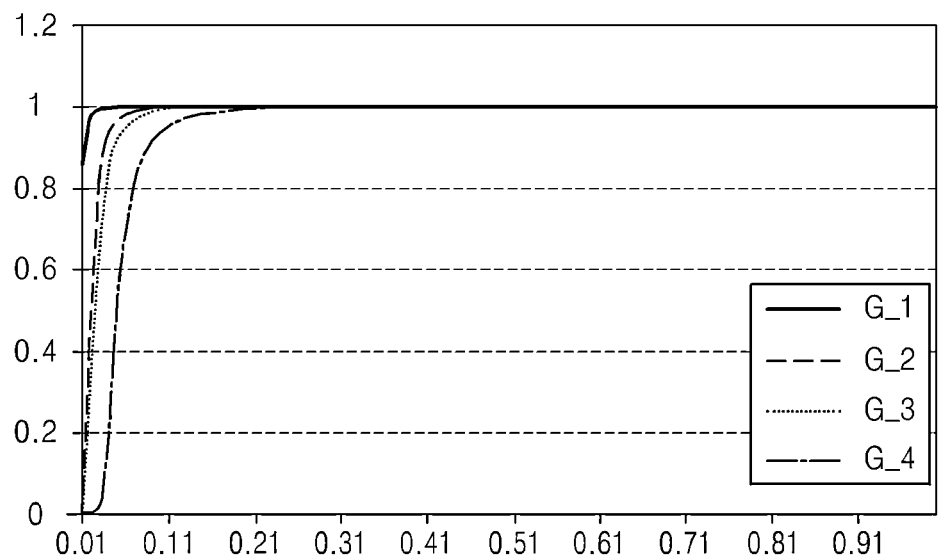
FIG. 12 is a graph illustrating an example of a shrinkage gain function for removing noise.
FIG. 13 illustrates an example of a spatial filter used for an edge enhancement process.

FIG. 12 is a graph illustrating an example of the shrinkage gain function for removing noise. G__1, G__2, G__3, and G__4 denote the shrinkage gain function with respect to the 4 bands LL, LH, HL, and HH in the level 1, respectively. The shrinkage gain function is obtained when pixel values, i.e., wavelet coefficients, of images of the 4 bands LL, LH, HL, and HH after the wavelet transformation of the reference ultrasound image are processed by a gray scale, wherein the horizontal axis indicates a gray scale from 0 to 1 and the vertical axis indicates a shrinkage gain function value.

In greater detail, the left side of the horizontal axis, i.e., the side close to 0, corresponds to a noise component, and the right side of the horizontal axis, i.e., the side close to 1, corresponds to an edge of a tissue component. The vertical axis indicates a shrinkage gain function value by which a wavelet coefficient is to be multiplied, wherein 1 is the largest value and 0 is the smallest value. As an extreme case, multiplying a wavelet coefficient by a shrinkage gain function value of 1 indicates that the wavelet coefficient is preserved, and multiplying a wavelet coefficient by a shrinkage gain function value close to 0 indicates that the wavelet coefficient is very small, i.e., that characteristics of a pixel corresponding to the wavelet coefficient are removed. That is, because a pixel having a value close to 0 in the gray scale corresponds to a noise component, a shrinkage gain function value of the pixel is set to a value close to 0, thereby shrinking a wavelet coefficient of the pixel by multiplying the wavelet coefficient of the pixel by the value close to 0. As a result, the wavelet coefficient is shrunk, and the noise component is removed.

In FIG. 12, G__1, which is leftmost in FIG. 12, almost always has 1 as a shrinkage gain function value because G__1 represents an image of the LL band having a minimal noise component, and accordingly G__1 is close to an original image and rarely has wavelet coefficients to be shrunk. On the contrary, in G__4, which is rightmost in FIG. 12, a shrinkage gain function value rapidly decreases when a value of the horizontal axis is less than 0.11. This is because G__4 represents an image of the HH band having a high noise component and pixels including the noise component are close to 0 in the gray scale. In this case, it is determined that pixels corresponding to a value less than 0.11 in the gray scale include the noise component, and wavelet coefficients of the pixels are shrunk to remove noise. By adjusting a value of α (α is a constant) in Equation 10, a curve of the shrinkage gain function in FIG. 12 is adjusted.

In operation 1105, the image manipulator 213 performs the edge enhancement process. This process is irrelevant to the noise removing process and is optional because this process is to improve image quality of an ultrasound image by sharpening an outline of a part corresponding to the edge of the tissue component. Although the edge enhancement process is performed before the noise removing process in this example, the edge enhancement process may be performed after the noise removing process.

The edge enhancement process is only performed on components in the low frequency band. That is, when the wavelet transformation is performed, the edge enhancement process is performed on images of the LL band in each level. An example of a spatial filter used in the edge enhancement process is a finite impulse response (FIR) filter for calculating a center pixel value of a window having a predetermined size by performing a predetermined calculation by weighting each pixel value of neighboring pixels with respect to the center pixel in the window. In this example, a weight of an edge enhancement filter used for the edge enhancement process may be set differently based on whether the edge of the tissue component is included by using the aggregated tissue edge image. That is, while a general spatial filter is considered as the edge enhancement filter, a weight of the edge enhancement filter may vary according to whether the edge of the tissue component is included by using the aggregated tissue edge image.

FIG. 13 illustrates an example of a spatial filter used for the edge enhancement process. As a simple example, a 3×3 spatial filter is shown in FIG. 13. A value a of the center of the 3×3 spatial filter may be set to a large value for parts corresponding to an edge of a tissue component or to a small value for parts not corresponding to the edge of the tissue component, by using the aggregated tissue edge image. When weights in the 3×3 spatial filter are applied to respective pixels in a 3×3 block of pixels, the parts corresponding to the edge of the tissue component have a large pixel value due to the large weight, and the parts not corresponding to the edge of the tissue component have a small pixel value due to the small weight. That is, by applying an edge enhancement filter in which a weight of an edge of a tissue component is significantly different from a weight of a non-edge of the tissue component, a pixel value difference between parts corresponding to the edge of the tissue component and parts not corresponding to the edge of the tissue component is large, resulting in sharpening of the parts corresponding to the edge of the tissue component.

In operation 1107, the image manipulator 213 performs a wavelet coefficient shrinkage process. A wavelet coefficient corresponding to each pixel in an image of a predetermined band is determined according to the wavelet transformation, wherein noise may be removed by shrinking the wavelet coefficients of pixels corresponding to the noise component.

Edge weights by which the wavelet coefficients are to be multiplied for the wavelet coefficient shrinkage process are calculated. An edge weight function may be obtained using the following Equation 11:

$$EW(x, y) = \left(\frac{EM(x, y)}{255}\right)^\beta \quad (11)$$

In Equation 11, EW(x,y) denotes an edge weight, and EM(x,y) denotes a pixel value at a position of the aggregated tissue edge image. Since a part corresponding to the edge of the tissue component has a bright color in the aggregated tissue edge image, the part corresponding to the edge of the tissue component has a value close to 255 as a pixel value, and since a part corresponding to noise has a dark color in the aggregated tissue edge image, the part corresponding to noise has a value close to 0. As a result, because the part corresponding to the edge of the tissue component has an edge weight set to a value close to 1, even a corresponding wavelet coefficient is multiplied by the edge weight, the corresponding wavelet coefficient is not largely affected. However, because the part corresponding to noise has an edge weight set to a value close to 0, when a corresponding wavelet coefficient is multiplied by the edge weight, the corresponding wavelet coefficient is significantly shrunk, resulting in removing the noise component.

Although the wavelet coefficient shrinkage process may be performed using only the edge weight function, the wavelet coefficient shrinkage process may be performed using a value obtained by multiplying the shrinkage gain function described above by the edge weight function.

Figure 14:
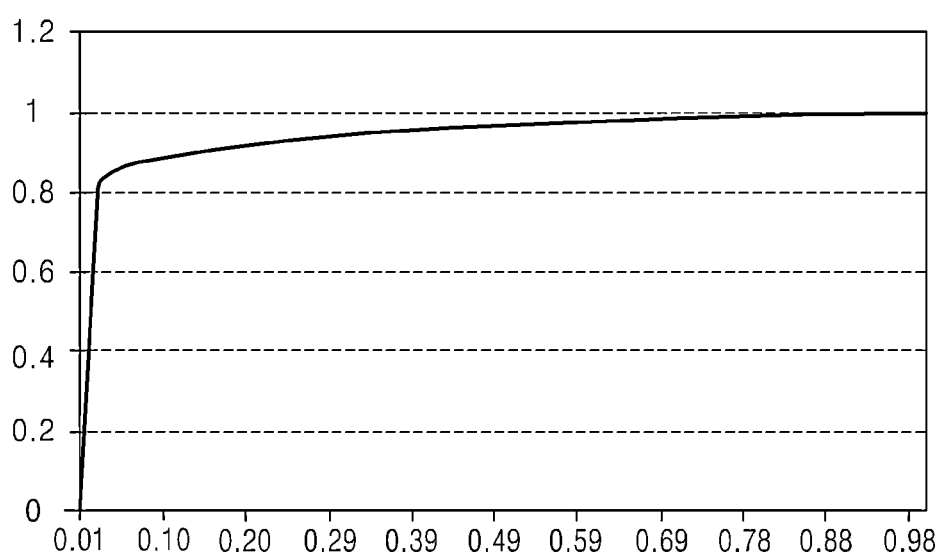
FIG. 14 is a graph illustrating an example of an edge weight function used for a wavelet coefficient shrinkage process.

FIG. 14 is a graph illustrating an example of the edge weight function used for the wavelet coefficient shrinkage process. The horizontal axis indicates a gray scale unit from 0 to 1, and the vertical axis indicates an edge weight from 0 to 1 as a value by which a wavelet coefficient is to be multiplied.

In greater detail, the horizontal axis indicates a pixel value from 0 to 255 with the gray scale from 0 to 1, wherein the left side of the horizontal axis that is close to 0 corresponds to a dark area, i.e., a homogeneous area, in the aggregated tissue edge image, and the right side of the horizontal axis that is close to 1 corresponds to a bright area, i.e., the edge of the tissue component, in the aggregated tissue edge image. For a vertical axis value corresponding to each horizontal axis value, because the side close to 0 in the horizontal axis, i.e., the homogeneous area in the aggregated tissue edge image, is an area from which noise is going to be removed, a value close to 0 is set as an edge weight with respect to the homogeneous area in the aggregated tissue edge image. On the contrary, a value close to 1 is set as an edge weight with respect to the side close to 1 in the horizontal axis, i.e., the edge of the tissue component in the aggregated tissue edge image. By adjusting a value $\beta$ ($\beta$ is a constant) in Equation 11, the curve of the edge weight function in FIG. 14 is adjusted.

The shrinkage gain function of FIG. 12 is obtained by obtaining gain values by which wavelet coefficients are to be multiplied based on wavelet-transformed band images, and the edge weight function is obtained by obtaining edge weights by which wavelet coefficients are to be multiplied based on the aggregated tissue edge image. In these two functions, the horizontal axis indicates the gray scale, wherein the left side in the horizontal axis corresponds to the homogeneous area including the noise component to be removed and the right side corresponds to the edge of the tissue component. As a result, the shape of the graph of the edge weight function is similar to that of the gain shrinkage function.

In operation 1109, the image manipulator 213 performs an inverse wavelet transformation process. That is, an image for which the wavelet coefficient shrinkage process has been performed is restored by performing the inverse wavelet transformation process. The inverse wavelet transformation process may also be repeatedly performed, and in this case, the inverse wavelet transformation process is repeatedly performed until the original ultrasound image size before the wavelet transformation was performed has been restored. Accordingly, an ultrasound image whose image quality has been enhanced is finally generated.

Figure 15:
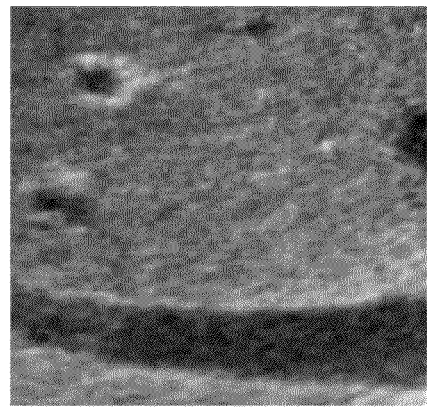
FIG. 15 illustrates an example of an original ultrasound image before a noise removing process.

FIG. 15 illustrates an example of an original ultrasound image before the noise removing process. A lot of noise in a bright speckle pattern exists around a predetermined tissue (a blood vessel located in the horizontal direction in FIG. 15) in an object to be diagnosed. Due to the noise, an overall image quality of the ultrasound image is bad, and an edge part of the object to be diagnosed is blurred.

Figure 16:
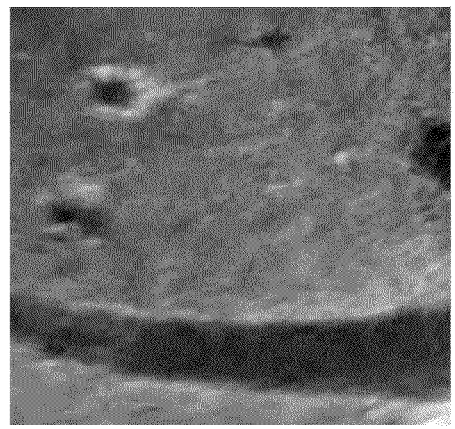
FIG. 16 illustrates an example of a resulting ultrasound image after the noise removing process has been performed by using an aggregated tissue edge image.

FIG. 16 illustrates an example of a resulting ultrasound image after the noise removing process has been performed by using the aggregated tissue edge image. FIG. 16 shows an ultrasound image corresponding to a result after noise existing in a non-edge area is removed by determining an edge of the tissue component in the object to be diagnosed in the original ultrasound image of FIG. 15 by using the aggregated tissue edge image. Comparing the resulting ultrasound image of FIG. 16 with the original ultrasound image of FIG. 15, the noise in the bright speckle pattern is remarkably reduced, thereby enhancing the overall image quality of the ultrasound image.

Figure 17:
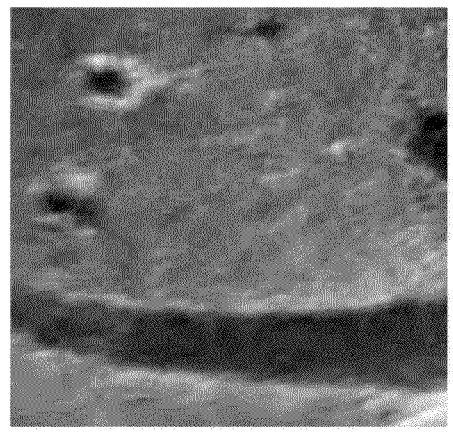
FIG. 17 illustrates an example of a resulting ultrasound image after the noise removing process and the edge enhancement process have been performed by using an aggregated tissue edge image.

FIG. 17 illustrates an example of a resulting ultrasound image after the noise removing process and the edge enhancement process have been performed by using the aggregated tissue edge image. FIG. 17 shows an ultrasound image corresponding to a result after the noise removing process and the edge enhancement process are performed with respect to the original ultrasound image of FIG. 15. Comparing the resulting ultrasound image of FIG. 17 with the resulting ultrasound image of FIG. 16, the edge of the tissue component is sharper in FIG. 17 than it is in FIG. 16

As described above, an ultrasound image having an enhanced image quality may be acquired by removing noise without damaging a tissue component in the ultrasound image.

The 3D ultrasound volume data detecting apparatus 110, the probe 112, the ultrasound image processing apparatus 120, the input unit 201, the image processor 203, the 2D image generator 205, the tissue edge image generator 207, the image quality enhancement processor 209, the aggregated tissue edge image generator 211, the image manipulator 213, the output unit 215, the storage unit 217, and the user interface 219 described above may be implemented using one or more hardware components, one or more software components, or a combination of one or more hardware components and one or more software components.

A hardware component may be, for example, a physical device that physically performs one or more operations, but is not limited thereto. Examples of hardware components include piezoelectric transducers, amplifiers, low-pass filters, high-pass filters, band-pass filters, analog-to-digital converters, digital-to-analog converters, data storage devices, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of processing an ultrasound image, the method comprising:
   generating a plurality of two-dimensional (2D) ultrasound images from three-dimensional (3D) ultrasound volume data of an object to be diagnosed;
   generating a plurality of tissue edge images of an edge of at least one tissue component in the object to be diagnosed based on values of a plurality of pixels forming each of the 2D ultrasound images generated from the 3D ultrasound volume data; and
   generating a 2D ultrasound image from which a noise component has been removed by discriminating the edge of the at least one tissue component from a position of the noise component based on a difference between a similarity of the edge of the at least one tissue component in the tissue edge images and a similarity of the noise component in the tissue edge images.

2. The method of claim 1, wherein the generating of the 2D ultrasound image from which the noise component has been removed comprises:
   identifying the edge of the at least one tissue component based on the difference between the similarity of the edge of the at least one tissue component in the tissue edge images and the similarity of the noise component in the tissue edge images;
   generating, from the tissue edge images, an aggregated tissue edge image from which the noise component has been removed; and
   removing the noise component from one of the 2D ultrasound images generated from the 3D ultrasound volume data based on the aggregated tissue edge image.

3. The method of claim 2, wherein the plurality of 2D ultrasound images comprise a reference ultrasound image from which the noise component is to be removed, and a first ultrasound image and a second ultrasound image adjacent to the reference ultrasound image; and
   the plurality of tissue edge images comprise a reference tissue edge image corresponding to the reference ultrasound image, and a first tissue edge image and a second tissue edge image adjacent to the reference tissue edge image.

4. The method of claim 3, wherein the generating of the aggregated tissue edge image comprises:
dividing the tissue edge image into blocks each having a predetermined size;
matching blocks in the reference tissue edge image with corresponding blocks in the first tissue edge image, and with corresponding blocks in the second tissue edge image;
discriminating blocks of the reference tissue edge image including the edge of the tissue component from blocks of the reference tissue edge image excluding the edge of the tissue component based on the difference between the similarity of the edge of the tissue component and the similarity of the noise component in the matching blocks;
removing the noise component from the blocks of the reference tissue edge image excluding the edge of the tissue component; and
aggregating the blocks of the reference tissue edge image including the edge of the tissue component and the blocks of the reference tissue edge image from which the noise component has been removed to generate the aggregated tissue edge image.

5. The method of claim 4, wherein the matching of the blocks comprises determining that a block in the reference tissue edge image matches a corresponding block in the first tissue edge image or the second tissue edge image if a normalized cross-correlation (NCC) indicating a similarity between the two blocks is greater than a threshold indicating that the two blocks match each other.

6. The method of claim 4, wherein the discriminating of the blocks comprises determining that a block in the reference tissue edge image includes the edge of the tissue component if a normalized cross-correlation (NCC) indicating a similarity between the block in the reference tissue edge image and a corresponding block in the first tissue edge image or the second tissue edge image is greater than a threshold indicating that the two blocks include the edge of the tissue component.

7. The method of claim 3, wherein the removing of the noise component comprises:
performing a wavelet transformation on the reference ultrasound image to obtain wavelet coefficients respectively corresponding to the pixels of the reference ultrasound image;
removing the noise component from the reference ultrasound image by the shrinking the wavelet coefficients respectively corresponding to pixels of the reference ultrasound image that correspond to pixels of the aggregated tissue edge image from which the noise component has been removed based on information about the pixels of the aggregated tissue edge image from which the noise component has been removed; and
performing an inverse wavelet transformation on the wavelet coefficients respectively corresponding to the pixels of the reference ultrasound image including the shrunk wavelet coefficients to restore the reference ultrasound image without the noise component.

8. The method of claim 7, wherein:
the wavelet transformation divides the reference ultrasound image into a plurality of band images in different frequency bands, and is repeatedly performed with respect to a band image in a low frequency band to divide the reference ultrasound image into a plurality of band images having a plurality of resolution levels: and
the inverse wavelet transformation is performed a same number of times as the wavelet transformation has been repeatedly performed.

9. The method of claim 7, wherein the shrinking of the wavelet coefficients comprises multiplying each of the wavelet coefficients by a respective edge weight in a range from about 0 to about 1 that is generated based on the aggregated tissue edge image.

10. The method of claim 9, wherein the shrinking of the wavelet coefficients further comprises multiplying each of the wavelet coefficients multiplied by the respective edge weight by a shrinkage gain function value in a range from about 0 to about 1 that is generated based on band images generated by the wavelet transformation.

11. The method of claim 7, wherein the removing of the noise component further comprises performing an edge enhancement to sharpen an outline of the edge of the tissue component in the reference ultrasound image based on information about pixels of the aggregated tissue edge image corresponding to the edge of the tissue component.

12. The method of claim 11, wherein the performing of the edge enhancement comprises applying an edge enhancement filter to the pixels of the reference ultrasound image, where a weight of the edge enhancement filter applied to pixels of the reference ultrasound image corresponding to the edge of the tissue component is different from a weight of the edge enhancement filter applied to pixels of the reference ultrasound image not corresponding to the edge of the tissue component.

13. The method of claim 1, wherein the plurality of 2D ultrasound images are adjacent to each other in 2D ultrasound images extractable from the 3D ultrasound volume data.

14. The method of claim 1, wherein the noise component comprises speckle noise generated by an interference phenomenon occurring between ultrasonic wavelengths.

15. The method of claim 1, wherein the generating of the plurality of tissue edge images comprises:
generating gradient images in vertical and horizontal directions for each pixel in each of the plurality of 2D ultrasound images;
generating a structure matrix for each pixel in each of the plurality of 2D ultrasound images based on the gradient images in the vertical and horizontal directions;
calculating eigenvectors having maximum and minimum variations and eigenvalues corresponding to the eigenvectors from the structure matrix; and
detecting the edge of the tissue component based on a difference between the eigenvalues.

16. The method of claim 15, wherein the detecting of the edge of the tissue component comprises detecting the edge of the tissue component when the difference between the eigenvalues is greater than a predetermined value.

17. A non-transitory computer-readable storage medium storing a program for controlling a computer to perform a method of processing an ultrasound image, the method comprising:
generating a plurality of two-dimensional (2D) ultrasound images from three-dimensional (3D) ultrasound volume data of an object to be diagnosed;
generating a plurality of tissue edge images of an edge of at least one tissue component in the object to be diagnosed based on values of a plurality of pixels forming each of the 2D ultrasound images generated from the 3D ultrasound volume data; and
generating a 2D ultrasound image from which a noise component has been removed by discriminating the edge of the at least one tissue component from a position of the noise component based on a difference between a similarity of the edge of the at least one tissue component in the tissue edge images and a similarity of the noise component in the tissue edge images.

18. An apparatus for processing an ultrasound image, the apparatus comprising:
   an input unit configured to receive three-dimensional (3D) ultrasound volume data of an object to be diagnosed;
   an image processor configured to:
      generate a plurality of two-dimensional (2D) ultrasound images from the 3D ultrasound volume data;
      generate a tissue edge image comprising an edge of a tissue component in the object to be diagnosed based on values of a plurality of pixels forming each of the 2D ultrasound images generated from the 3D ultrasound volume data; and
      removing a noise component from the tissue edge image based on a difference between a similarity of the edge of the tissue component and a similarity of the noise component in the tissue edge images; and
   an output unit configured to output the 2D ultrasound image from which the noise component has been removed.

19. The apparatus of claim 18, wherein the image processor comprises:
   a 2D image generator configured to generate the plurality of 2D ultrasound images from the 3D ultrasound volume data;
   a tissue edge image generator configured to generate the tissue edge image;
   an aggregated tissue edge image generator configured to:
      identify the edge of the tissue component based on the difference between the similarity of the edge of the tissue component in the tissue edge images and the similarity of the noise component in the tissue edge images; and
      generate, from the tissue edge images, an aggregated tissue edge image from which the noise component has been removed; and
   an image manipulator configured to remove the noise component from one of the 2D ultrasound images generated from the 3D ultrasound volume data based on the aggregated tissue edge image.

20. The apparatus of claim 19, further comprising a storage unit configured to store all kinds of images generated by the image processor.

* * * * *